United States Patent [19]
> Block

[11] 3,975,084
[45] Aug. 17, 1976

[54] PARTICLE DETECTING SYSTEM
[75] Inventor: Myron J. Block, Nahant, Mass.
[73] Assignee: Block Engineering, Inc., Cambridge, Mass.
[22] Filed: Aug. 19, 1974
[21] Appl. No.: 498,382

Related U.S. Application Data
[63] Continuation-in-part of Ser. No. 401,207, Sept. 27, 1973, abandoned.

[52] U.S. Cl.............................. 356/103; 250/574; 356/244; 240/2 M; 350/87; 350/91
[51] Int. Cl.².................... G01N 21/00; G02B 21/06
[58] Field of Search ........... 250/458, 574; 356/102, 356/103, 39, 244, 246; 240/2 M; 350/87, 91, 235

[56] References Cited
UNITED STATES PATENTS
3,542,482  11/1970  Wilks, Jr............................. 386/244
3,604,927  9/1971  Hirschfeld............................ 356/244
3,720,470  3/1973  Berkhan............................... 356/103

*Primary Examiner*—John K. Corbin
*Assistant Examiner*—Conrad Clark
*Attorney, Agent, or Firm*—Schiller & Pandiscio

[57] ABSTRACT

Submicron-sized particles are detected by a system which observes emission, as by scattering or by fluorescence from particles undergoing Brownian motion in a region of a fluid medium excited by an evanescent wave created adjacent an interface between the fluid medium and a multiple internal totally reflecting cell or light guide. The excited region can range in depth between several wavelengths and a fraction of the wavelength of the exciting beam, hence serves as an "aperture" having a dimension of about the same order of magnitude as the particles being detected. The particles can be classified according to size by examining the amplitude modulation arising out of the motion of the particles through the aperture.

22 Claims, 5 Drawing Figures

PARTICLE DETECTING SYSTEM

This application is a continuation-in-part of U.S. patent application Ser. No. 401,207 filed Sept. 27, 1973, now abandoned.

This invention relates to optical systems and more particularly to the detection and classification of submicron-dimensioned particles, such as viruses, suspended in a fluid medium.

The detection and classification of submicron-dimensioned particles, particularly viruses, have long been an important goal frustrated by a number of vexing problems. One standard approach has been through electron microscopy, which cannot readily be used with free floating or "live" specimens, and requires elaborate, time-consuming sample preparation and very complex, expensive equipment.

Generally, optical microscopes have found very limited use because the viral particles are dimensioned well below the resolution limits of the microscope.

Additionally, imaging optics at very high magnifications have a depth of field which is severely limited, for example, to a few microns. Absorption and scattering from the out-of-focus particles or structures in the field of viewing tend severely to reduce contrast and make it very difficult to distinguish particles which are truly in focus, i.e. the signal-to-noise ratio is very poor. An optical system however, is known in which minute particles suspended in a fluid medium are illuminated with coherent light. Back-scattered light from the particles is then observed by heterodyne spectrometry to obtain data on the Brownian motion of the particles, which motion can then be correlated with the particle sizes. Briefly then, it is known to measure particle size by determining the Doppler broadening of scattered light. The observed frequency distribution of particle velocities is described by a Lorentzian curve or function, the half-width of which is proportional to the particle size. There are a number of disadvantages to this technique. First, it requires the use of coherent radiation so that one can measure the comparatively slow Brownian velocities. Additionally, since the scattering from all particles is recorded, there is no discrimination between types of particles. This occurs because the sum of a plurality of Lorentzian function is difficult to resolve into its components, and thus it is difficult to resolve the particles into constituent sizes where there is a range of particle types. Further, the amount of light scattered by a particle is proportional to the sixth power of the particle diameter, so the signals from big particles tend to swamp out the signals from small particles.

In copending application Ser. No. 375,807 filed by Tomas Hirschfeld on July 2, 1973, and commonly assigned with the present application, there is disclosed a system which obviates some of the above-noted difficulties in heterodyne spectroscopy. The Hirschfeld invention makes use of fluorescent staining to differentiate between different particle types. Since fluorescent emission is broad band and not narrow band, the use of Doppler broadening as a size discriminant is not feasible. Instead, the Hirschfeld system makes use of a spatial filter, such as an aperture, to modulate fluorescent emission from the particles to produce a fluctuation spectrum which is a function of the velocities of the fluorescing particles. Except in respect to discrimination between different types of particles by fluorescence methods, the Hirschfeld technique is subject to many of the disadvantages of the Doppler scattering method. For example, a regular aperture has edges which are $sinc^2$ (i.e. $\sin x^2/x$ ) in nature. Convolution of random motion and such $sinc^2$ wave edges will result in a Lorentzian curve. If several sizes of particles are being observed simultaneously, the observed signal as previously noted will be the sum of several Lorentzian curves which is difficult to resolve into its component functions. With the Hirschfeld system, the optimum aperture for sizing viruses with reasonable accuracy would be roughly 1/10 of a wavelength. Such aperture clearly cannot be attained with standard optical techniques because of diffraction limitations. Additionally, the use of a single small aperture leads to observation of a correspondingly small volume of sample fluid, so that if measurements of the particles in the fluid are to be made within a reasonable time span, a high particle density is required. In using the Hirschfeld system for fluorescence microscopy, existing techniques illuminate a considerably larger volume of material than that which is in critical focus at any one time. Thus, if only with respect to fluorescent emissions, there will tend to be a high background level due to the presence of the fluorescent dye itself in solution and the presence of out-of-focus dyed particles. As earlier observed, this high background level will lead to low contrast.

A principal object of the present invention is therefore to obviate a number of the problems above delineated, and particularly those associated with the Hirschfeld system.

Other important objects of the present invention are to provide apparatus for and method of detecting submicron-dimensioned particles with substantially improved supression of background emission; to provide such a system which employs spatial filtering to obtain a repetition rate spectrum of particle velocities, wherein the spatial filter has an effective aperture with a dimension substantially less than the wavelength of the viewing radiation, and to provide such an apparatus which is simple and comparatively inexpensive compared to the prior art.

To effect the foregoing and other objects of the present invention, the invention employs a phenomenon known as evanescent or inhomogenous waves. According to Snell's Law, when a light beam, traveling in a first medium of a given refractive index, impinges upon an interface between the first medium and a second medium having a different index of refraction, at an angle of incidence greater than the critical angle, so-called total reflection of the beam will occur. However, the incident beam will also set up an inhomogeneous optical surface wave in the second medium. This latter wave, termed an evanescent or lateral wave, propagates parallel to the reflecting interface and its field strength attenuates exponentially in a direction normal to the interface. If the second medium is non-absorbent, the energy in the evanescent wave eventually returns to the reflected beam in the first medium, thus making the reflection truly total. If the second medium is absorbent, some of the evanescent wave energy will be absorbed and the reflection is not truly total. This phenomenon arises when light traverses a multiple attenuated total reflection plate or cell and hence is also known as the ATR phenomenon. The same phenomenon arises with light traversing a waveguide or light guide such as a film of light transmissive material having a thinness around the order of the wavelength of the light. The ATR phenomenon was first applied in 1959 by Fahrenfort who measured the energy in the reflected beam to determine the extent of absorption by a sample which constituted the second medium. ATR has since been widely used in analytical systems, as described in N. J. Harrick "Internal Reflection Spectroscopy" New York, Interscience, 1967. ATR in light guides and systems for coupling such light guides to light sources are described by P. K. Tien in "Light Waves in Thin Films and Integrated Optics", *Applied Optics*, Nov. 1971, pp. 2395-2413.

The sample of particles in a fluid medium is initially prepared to limit the population to the desired particles. Thus, for example, the sample is stained with a complex, nucleic acid-specific stain, which selectively fluorochromes all nucleic acid-containing particles and molecules. In a biological sample, the stained particles will include whole cells, mitochondriae, chromosomes, ribosomes, messenger and transfer RNA as well as viruses. The first three, being much larger in size than even the largest viruses, may be efficiently rejected by filtering the sample through a Millipore filter; the last two, much smaller in molecular weight than the smallest viruses, can be wholly eliminated by rapid dialysis in a hollow fiber. Thus there is provided a sample in which the only fluorescent particles are the viruses, ribosomes, the very largest messenger RNA and some fragments of larger particles.

This sample is placed to provide an interface with an ATR cell or a thin film light guide and exciting radiation directed into the cell or film creating an excited zone or region in the sample. As Browian motion lets the particles drift through this region, substantially complete modulation of their emission takes place over a few hundred A of travel. The sharpness of the boundary of the region is such that modulation frequencies, derived by autocorrelation of the outwardly random noise in the signal, go from 0 to 1 kHz for the 180-3500 A virus size range.

By now computing, in appropriate instrument circuitry, the log-log fast Fourier transform of the autocorrelation curve of the signal-averaged AC component of the fluorescent signal, one obtains a straight line graph the slope of which is proportional to the particle hydrodynamic radius, and the intercept of which is proportional to the product of the particle concentration times the particle nucleic acid content.

Other objects of the invention will in part be obvious and will in part appear hereinafter. The invention accordingly comprises the apparatus possessing the construction, combination of elements, and arrangement of parts and the process including the several steps and the relation of one or more of such steps with respect to each of the others, all of which are exemplified in the following detailed disclosure and the scope of the application of which will be indicated in the claims.

For a fuller understanding of the nature and objects of the present invention, reference should be had to the following detailed description taken in connection with the accompanying drawings wherein.

Figure 1:
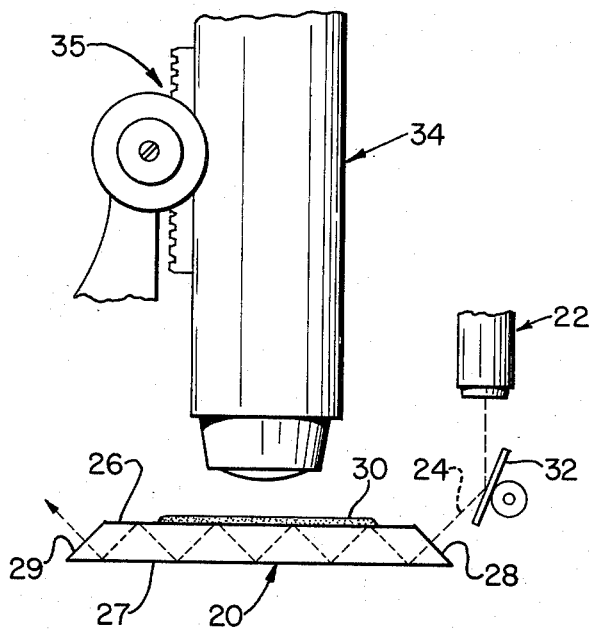
FIG. 1 is a schematic elevational view, partly in fragment, of an exemplary device embodying the principles of the present invention.

Referring now to FIG. 1 of the drawing there is shown a device embodying the principles of the present invention and comprising total internally reflecting means or light guide, both represented by cell 20. As one condition for obtaining an evanescent wave, cell 20 must provide an optical path through material having a greater refractive index than the range of indices of the fluid media which support the particles being examined. The material of cell 20 must also be transparent over the wavelength range of the exciting beam of radiation and should possess appropriate physical and chemical stability with respect to both the exciting radiation and the fluid medium which is employed to form an interface with the cell. Among the typical materials which may be used are glasses such as crown glass and flint glass, quartz, fused silica, and synthetic organic polymers such as polystyrene and polymethylmethacrylate.

The system of the invention preferably includes source 22 which provides beam 24 of radiation, typically within a selected narrow band of wavelengths, which can be varied at will. While the present invention does not depend upon Doppler shifting and in that respect coherent illumination is not required, as will be seen later, advantage can be taken of fluorescence phenomena and therefore it may be desirable to provide the exciting beam at a comparatively narrow band of wavelength, which differs substantially from the wavelength band of the excited fluorescent emission. Hence, source 22 is typically a monochromator or preferably is a laser to provide a high intensity source, a particularly desirable feature in view of the minuteness of the particles being sought. The monochromator usually includes means for collimating output beam 24 which is also a desirable feature to maintain total reflection.

While cell 20 can assume a number of configurations, as shown in FIG. 1, a preferred embodiment (with thickness exaggerated for clarity) of a total reflection cell comprises a rectangular flat sheet or thin film of material transparent to beam 24, the largest opposed sides or surfaces 26 and 27 of the sheet being substantially plane and parallel with one another. Optimally, surfaces 26 and 27 are optically plane so as to minimize the amount of light leakage therethrough due to minute imperfections which might cause the angle of incidence of a reflecting beam to exceed the critical angle at the imperfection. Typically, cell 20 will approximate a 3 × 1 inch silica microscope slide of about 1 mm thickness. Opposed edges 28 and 29 of cell 20 are polished and beveled at angles judiciously chosen with respect to the critical angles for internal reflection and to the length of the slide so that a proper path length can be provided to achieve internal multiple total reflection between edges 28 and 29 with the beam entering one of the latter edges approximately normal to its surface and leaving the other of the edges in a similar manner.

Alternatively, as well known to those skilled in the art, one of surfaces 26 or 27 can have formed thereon or cemented thereto by an appropriate optical cement of the proper index of refraction, a prism which then constitutes the input face into which the excitation beam 24 can be introduced.

As previously noted, an evanescent wave formed, for example at the interface where surface 26 contacts fluid medium 30 is exponentially attenuated in the direction normal to this boundary or interface. For existing optical materials, at practical illumination geometries, the depth of the zone or region so illuminated can be a minimum as small as 1/20 of a wavelength, much less than the diffraction limited resolution possible for an ordinary light wave. At the same time, the illuminated region, due to waveguiding along the surface, is several mm$^2$ in area, even while only 250 or so Å in thickness. The distance (1/e) that the wave penetrates effectively into the fluid medium can be varied between the above noted minimum and several wavelengths, by changing the angle of incidence of the internally multiply reflected beam within cell 20 particularly close to the critical angle. To this end, the system of the present invention may include tuning means shown in simplest form as rotatable mirror 32 disposed between input edge 28 or cell 20 and the output from radiation source 22 so as to vary the angle at which beam 24 enters with respect to the surface of edge 28. If the incoming beam at edge 28 is comparatively wide band it should be introduced as close as possible to normal to the surface of edge 28 in order to avoid chromatic dispersion of the beam. Hence, as previously noted, it is desirable to use a narrow band or monochromatic beam of radiation so that, if one wishes to tune the ATR cell with respect to the effective depth of penetration of the evanescent wave, the input beam to edge 28 can be introduced at variable angle without regard to any chromatic effects.

Disposed, as shown in FIG. 1, adjacent surface 26 upon which a layer of the sample fluid medium 30 has been placed are means for detecting radiant emission from the particles moving in and out of the evanescent wave. Preferably, such means are imaging optics, such as microscope 34 (shown only in fragment). It will be appreciated that the particular type of optical system employed is not critical and therefore both refractive and reflective optics can be employed. Where the optics are imaging optics, it is preferred that it includes means, shown as rack and pinion 35, for focussing the optical system. Thus, the first conjugate plane (i.e. object plane) of the optical system (assuming an anastigmatic system) which is or can be made substantially coplanar with the region (hereinafter referred to as the excited region) in the fluid medium traversed by an evanescent wave formed responsively to passage of exciting beam 24 through cell 20 by multiple total internal reflection.

In operation, light (which term is intended to include radiation from the ultraviolet into the infrared) is diverted by mirror 32 at an appropriate angle into edge 28 of cell 20. A sample of fluid medium 30, containing particles to be detected, is placed as shown on upper surface 26 of cell 20. Thus, the cell is illuminated by beam 24 so that total internal multiple refraction occurs within the cell at the interface between surface 26 and fluid medium 30. As noted, the evanescent wave produced by the reflections of beam 30 propagates parallel to surface 26 and is exponentially attenuated in medium 30 from the interface between the medium and cell 20. The Brownian motion of small particles in medium 30 will move the latter in and out of the excited layer region in medium 30 in which the evanescent wave has a substantial field intensity. As the particles are observed or detected by microscope 34 either through scattering of the evanescent wave or by fluorescence excited in the particles by the evanescent wave, the emission from particles will be modulated, i.e. appear to scintillate, the scintillation duration being established by the length of time that the particles remain in the excited region within medium 30. Particles outside of the excited region will of course not emit radiation and hence will not be visible.

It should be noted that the excited region then functions as an "aperture" only one of the dimensions of which (i.e. the thickness) is extremely small. This effective "aperture" dimension is, as noted, smaller than the resolving power of any imaging optical system, for it is necessarily below the diffraction limit. However, since only one dimension of the excited region in medium 30 is small, a reasonably sizable volume may be achieved. For example, if the 1/e thickness of the excited region is 1/10 of a wavelength and imaging optical system 34 is a standard optical microscope, the field of view of the microscope objective will emcompass a portion of the excited region which will typically be a few hundred cubic microns in volume. Thus, high particle concentration in the fluid medium is not necessary to obtain a statistically valid sampling of particle signals in a reasonably short time because the volume which is imaged by optical system 36 is relatively large. Also the function 1/e is self-apodizing hence the resolution obtainable is greater than that which could be expected from apertures of similar size but not apodized.

It should be noted that "aperture" portion of the excited region discriminates against large particles since only a small part of such a large particle can be in the excited region at any one time. Thus, the large particles will not produce signals which would tend to swamp out the signals due to small particles. It should be noted that the excited region is immediately contiguous to a physical boundary, and thus the illumination provided by the evanescent wave is confined principally to stagnation layer in the fluid medium; thus the effect of convection currents on the particles, a problem in well slides, is greatly reduced in the present invention. Because the excited region is so thin, the average dwell time for particles moving by Brownian motion through the region is very short; this leads to a relatively high frequency of modulation of the amplitude of the light signals from the particles. Because of this high frequency imposed by the ATR "aperture" the relatively low frequency signal that would result from the rotation of an elongated particle can be effectively discriminated against.

Another type of discrimination against an unwanted effect lies in the fact that in ATR illumination, the Poynting vector lies parallel to the surface. Thus, photophoresis is minimized as a perturbing effect inasmuch as the photophoretic induced motion is parallel to the interface rather than normal to it, while the "aperture" serves to provide maximum modulation of the signal from a particle moving in a direction normal to the interface.

In one aspect of the invention, the sample fluid is treated with one or more fluorescent dyes which are specific to particles or constituents of particles. For example, one can dye the nucleic acids of viral particles with a number of dyes which will fluoresce when appropriately excited. For such purpose, one can use such well known dyes as acridine orange, quinacrine mustard, ethidium bromide, pyronine B, aurophosphine, euchrysine 2GNX, vesuvin, rhodamine S, rhodamine B, rhodamine 6G, coriphosphine O, civanol, acrifalvine, atabrine, phosphine, benzoflavine, rheonine A, thioflavine T, barberine, and many other like compounds. Input beam 24 is then preferably limited to wavelengths which are within the absorption band of the particular dye employed. The evanescent wave will excite fluorescence in the molecules in the dye dispersed thinly through fluid medium 30, but only in excited region of the latter, and will also excite fluoescence in the dye concentrations in the dyed particles present in the excited region of medium 30. It should be noted that with respect to dyed particles particularly, the thinness of the "aperture" or excited region, together with the movement of the particles lead to considerably less bleaching and other photochemical reactions, since the particles are not in the beam all of the time as they are in the heterodyne method.

Figure 2:
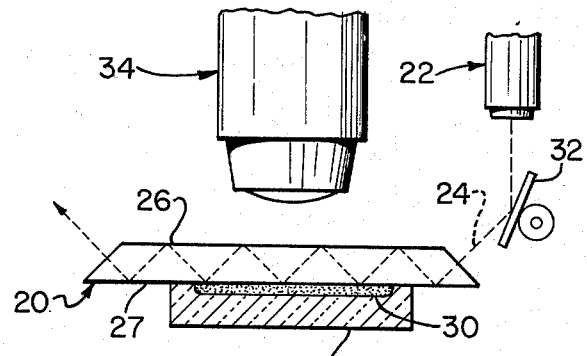
FIG. 2 is a schematic elevational view, partly in fragment, of an alternative exemplary device embodying the principles of the present invention.

In an alternative embodiment of the invention, as shown in FIG. 2, the interface between sample fluid medium 30 and ATR cell 20 is formed on the bottom surface 27 of cell 20 rather than on the upper surface of the latter. This is done typically by placing a well-slide or other container 36 below the ATR cell and filling container 36 with sample fluid 30. In the structure of FIG. 1, it will be seen that fluorescence arising within the excited region of medium 30 has to pass through the remainder of the fluid medium before it is collected by microscope 34, and if the fluid medium is turbid or is otherwise absorptive within the emission bandwidth of the fluorescing particles, the fluorescent signals will be attenuated. On the other hand, because in the embodiment of FIG. 2 imaging optics 34 views the excited region in sample 30 through the ATR cell, fluorescent emission arising in the excited region of medium 30 is not subject to nearly as much of such absorption, the bulk of the body of fluid medium 30 being thus disposed out of the path of radiation between the excited region and viewing optics 34.

The detection of the scintillating particles can of course be achieved simply by observing the scintillations through the eyepiece of microscope 34. However, the value of such observation is substantially limited to determining whether or not pertinent particles are or are not present. For example, if one dyes a sample with a dye specific to a nucleic acid, excites the sample with the evanescent wave of light of an appropriate wavelength, and observes the excited region of the sample through appropriate viewing optics filtered to see only the wavelengths of expected fluorescence, then the absence or presence of viral particles can be established. However, discrimination among the particles as to size cannot readily be accomplished by mere visual observation.

Figure 3:
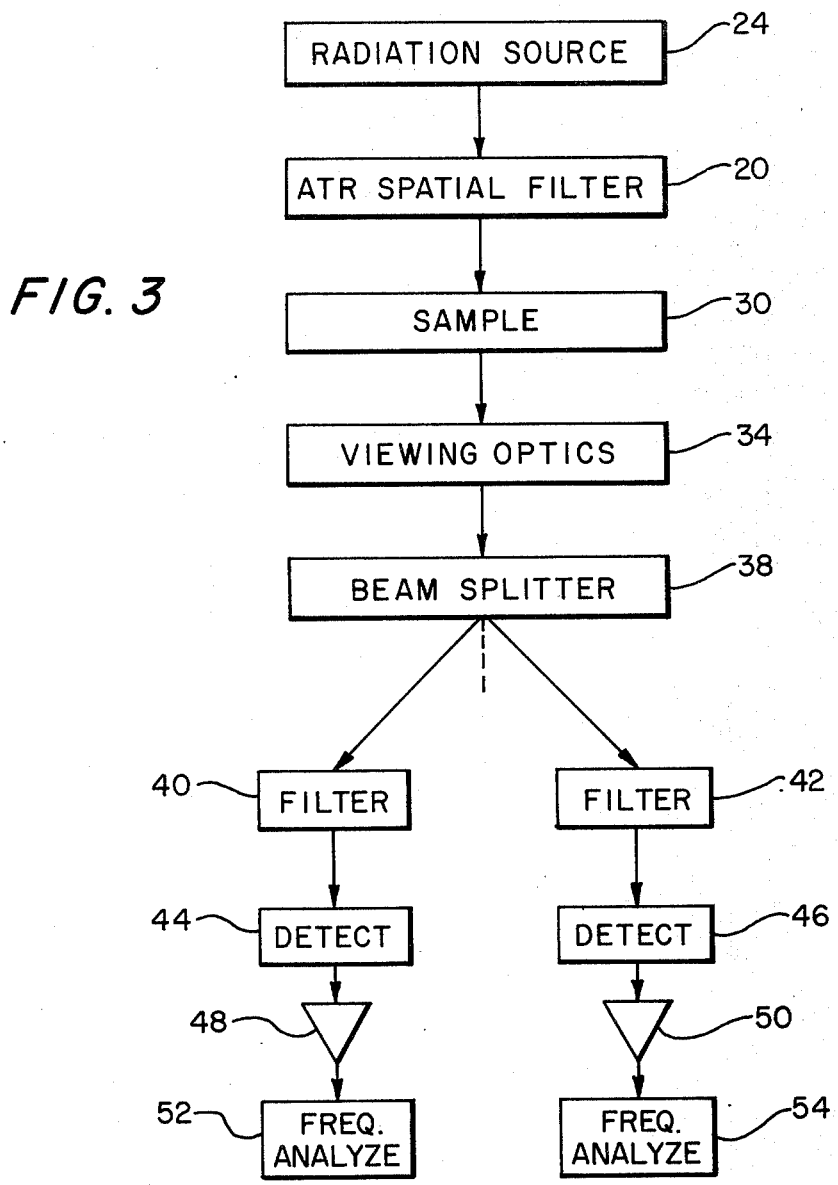
FIG. 3 is a block diagram of apparatus for the detection and classification of particles such as viruses.

Thus, as shown in FIG. 3, apparatus of the Hirschfeld type, modified in accordance with the present invention, is preferably employed to achieve size discrimination. Referring particularly to FIG. 3, wherein like numerals denote like parts, there will be seen radiation source 24 for projecting light through a spatial filter in the form of ATR cell 20. The embodiment of FIG. 3 also includes conventional optics 34 for detecting light arising in an excited region of sample fluid medium 30 and for directing such light onto beam splitter 38 to be divided into two or more beams which are respectively passed through wavelength filters 40 and 42 and thence to corresponding detectors 44 and 46. Filters 40 and 42 serve to limit the effective spectral bands seen by detectors 44 and 46 so that the system can discriminate between fluorescence arising from particles which have different dye affinities. For example, it is known that viruses consist essentially of either deoxyribonucleic acid or ribonucleic acid, usually surrounded by a protein shell, and that such nucleic acids can be dyed by certain unique dyes each providing a characteristic fluorescent emission spectrum quite distinct from one another. Detectors 44 and 46 typically are photoelectric cells such as photovoltaic or photoresistive devices which provide an electrical signal proportional to the amplitude of the light intensity incident thereon, and which are capable of responding, with extremely fast rise and decay times. The outputs of detectors 44 and 46 are connected to corresponding amplifiers 48 and 50, the outputs of which are connected to known types of frequency analyzers 52 and 54 more fully described hereinafter. The frequency analyzers are preferably synchronized such as by a common clock circuit associated therewith. The output of the frequency analyzer can be observed visually or preferably by automatic recording on strip charts, or are fed into computers for further processing.

In operation of the system of FIG. 3 it will be apparent that the signals seen by detectors 44 and 46 are modulated by the motion of the light emitting particles in the excited region of fluid medium 30 in a direction having a component normal to the interface between fluid medium 30 and ATR cell 20. The modulation essentially appears in the form of light pulses, each pulse representing the existence of a particle, and the pulse width being indicative of the dwell time of the particle in the excited region. It should be appreciated that the one "edge" of the ATR "aperture" in the boundary or interface is formed by a surface of cell 20, hence particles will not cross that "edge". The other or open "edge" of the ATR "aperture" is the field of the evanescent wave, the strength of which drops off exponentially from the interface. Hence, as a particle crosses this latter edge into or out of the excited region the intensity of emission from the particle will rise or drop exponentially as the case may be. The pulse generated by each particle as it moves through the aperture will thus have exponential rise and decay slopes.

Detectors 44 and 46 will each see an itensity spectrum of light from a multiplicity of particles moving in the excited region, which light is a summation of all the pulses within a particular band of wavelengths, each of which pulses has pulse edges which vary exponentially according to the velocity of the corresponding particle across the open edge. The sharpness of the open edge or boundary is such that modulation frequencies, derived by autocorrelation of the outwardly random noise in the signal, range from 0 to 1 kHz for the 180–3500 A virus size range. The output signal provided by each detector, is then subjected to a Fourier transformation which is performed in the corresponding one of frequency analyzers 52 and 54. The respective outputs of the latter when recorded or plotted graphically are then curves in terms of the modulation frequency vs. a function of the signal intensity.

Figure 4:
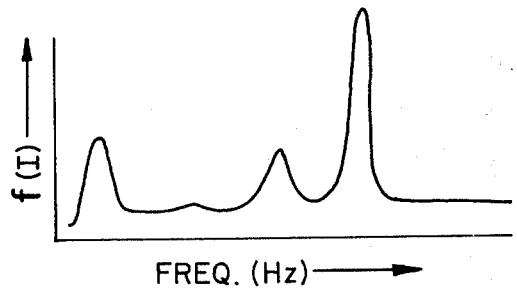
FIG. 4 is an exemplary plot of the signal derived from the device of FIG. 1.

A typical plot of the output of one of frequency analyzers 52 or 54 shown in FIG. 4 includes a number of peaks, the location of each of which is proportional to the equivalent diffusional diameters of various particles. The peak height and area are proportional to the quantity of the particle present of the size indicated by the location of the peak. Such a plot, first obtained with a variety of particles of known sizes, is used to calibrate the system, so that the location of peaks in plots made of samples of particles of unknown size can be appropriately identified as to size.

Other frequency analysis methods can be used of course. For example, a somewhat more sophisticated system involves inserting a correlator to autocorrelate the output from the detector prior to frequency analysis. Thus, the frequency analyzer will make a Fourier transform of the autocorrelation function. Upon linearizing that Fourier transform, the resulting data can be quite easily interpreted. For example, one can use the system disclosed by D. S. Thompson in his article "A Simple Method for Analyzing an Inelastic Light Scattering Spectra", Rev. of Scientific Instruments, Volume 41, pp. 1228-1229, August 1970.

In addition to the advantages earlier noted, there are several other aspects of the present invention which are of interest. For one, the field strength of the evanescent wave in free space is higher than that of the exciting beam, and in essence a gain is provided. Another way of asserting the foregoing is that the beam cross-section is effectively compressed although power is conserved, and the intensity therefore required of the illumination source in order to achieve a given signal from a small particle is reduced. Additionally, the use of the ATR cell allows one to use dark-field illumination miscroscope objectives for numerical apertures above the present practical limit of about 1.2. This is because in present dark field systems the condenser, working at its highest numerical aperture, must illuminate a ring or cone of light smaller than that which would be accepted by the numerical aperture of the microscope. An immersed condenser is capable of forming a cone of illumination with NA of about up to 1.4. Only the outer edge of the microscope field can be observed while the inner part of the condenser field must be obscured. This severely restricts the largest numerical aperture which can be used with the microscope condenser as well as the solid angle of collection of the objective lens. In the present invention, illumination is effectively in the form of a flat sheet of minute thickness, i.e. the excited region so that, to observe dark field one can use a microscope with the largest available numerical aperture.

Figure 5:
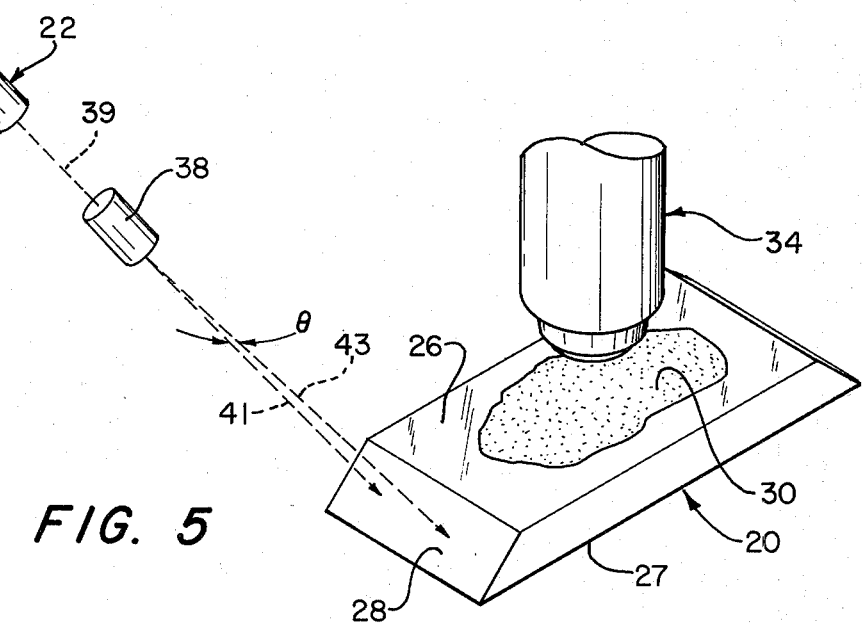
FIG. 5 is a schematic perspective view, partly in fragment, of yet another alternative device embodying the principles of the present invention.

As has been noted, modulation in the present invention arises out of the motion of the particle in a direction having a component moved to the ATR interface. However, if it is desired, one can also achieve modulation in the other axes (i.e. parallel to the ATR interface). Apparatus for accomplishing this end, as shown in FIG. 5 (wherein like numerals denote like parts) includes the same ATR cell 20, source 22, medium 30 and imaging optics 34 as the embodiments of FIGS. 1 and 2. However, beam splitting means shown generally at 38 are provided for dividing output beam 40 from source 22 into two beams 42 and 44 which lie in a common plane but diverge or converge from parallelism with one another by some small angle $\theta$. Beam splitting means 38 preferably is adjustable so that $\theta$ can be varied. The beams are both directed into edge 28 of cell 20 so as to impinge on surface 27 of the latter at the same angle of incidency.

For the apparatus of FIG. 5 source 22 should provide a beam of monochromatic radiation. It will then be appreciated that because of the angular separation between beams 42 and 44, the two beams will be temporally coherent and will provide an interference pattern within cell 20. However, more importantly (for the interference pattern in cell 20 will not provide effects observable by optics 34) the evanescent waves produced by each of beams 42 and 44 will interfere with each other, creating an interference pattern of excited and non-excited particles in the region of medium 30 into which the evanescent waves penetrate. Because the evanescent waves are slow waves, the interference pattern which can be produced from them can have dimensions in the order of a fraction of a wavelength of the original exciting radiation. The spacing in the pattern can be varied by changing $\theta$. A particle, moving parallel to the plane of the interface and within the field of the evanescent waves, will then be successively excited and non-excited by the field depending on the nature of the interference pattern and the excited emission from the particle will be correspondingly modulated.

Since certain changes may be made in the above apparatus and processes without departing from the scope of the invention herein involved, it is intended that all matter contained in the above description or shown in the accompanying drawing shall be interpreted in an illustrative and not in a limiting sense.

What is claimed is:

1. Apparatus for detecting submicron dimensional particles in a fluid medium, said apparatus comprising, in combination:
   a totally internally reflecting cell bounded at least in part by an interface with said medium; and
   imaging optical means including means for focussing said optical means so that the first conjugate plane thereof is substantially coincident with the region of said medium traversed by an evanescent wave formed upon internal reflection of an exciting beam of radiation within said cell.

2. Apparatus as defined in claim 1 wherein said first conjugate plane is coincident with said region.

3. Apparatus as defined in claim 1 including means for detecting, with respect to particles in Brownian motion in said region, intensity modulation of radiation emitted by said particles responsively to said wave.

4. Apparatus as defined in claim 3 including means for frequency analyzing said modulation.

5. Apparatus for detecting submicron-dimensioned particles in a fluid medium, and comprising in combination;
   a totally internally reflecting cell bounded at least in part by a surface for forming an interface with said medium, said cell being formed of a material having a higher refractive index than said medium;
   means for detecting radiant emission from particles in Brownian motion in the region of said medium adjacent said interface and traversed by evanescent waves formed upon passage of totally reflected illumination through said cell; and
   means for frequency analyzing the modulation of said radiant emission created by said motion of said particles across the boundary of said region.

6. Apparatus as defined in claim 5 wherein said means for detecting comprises a microscope.

7. Apparatus as defined in claim 5 including means for directing a beam of said illumination into said cell at an adjustable angle with respect to said interface.

8. Apparatus as defined in claim 5 wherein said cell is disposed between said means for detecting and said region.

9. Apparatus as defined in claim 5 wherein said region is disposed between said cell and said means for detecting.

10. Apparatus as defined in claim 5 including means for wavelength filtering radiant emission from said particles prior to detecting said emission.

11. Apparatus as defined in claim 5 including a source of said illumination.

12. Apparatus as defined in claim 11 wherein said source provides substantially monochromatic illumination.

13. Apparatus for providing modulated radiation emission from particles moving in a fluid medium, said apparatus comprising in combination,
   a totally internally reflecting cell bounded at least in part by a surface for forming an interface with said medium, and
   means for providing a pair of coplanar beams, each being temporally coherent and forming an angle with respect to one another in their common plane, said means being positioned with respect to said cell so that said beams can traverse said cell by total internal reflection, at least in part, from said surface at substantially the same angle of incidence.

14. Apparatus as defined in claim 13 including means for detecting radiant emission from particles in Brownian motion in the region of said medium adjacent said interface.

15. Apparatus as defined in claim 13 including means for variably adjusting the magnitude of said angle.

16. Apparatus as defined in claim 13 wherein said beams are both substantially monochromatic at substantially the same wavelengths.

17. Apparatus as defined in claim 13 wherein said means for providing said beams comprises a source of substantially monochromatic radiation and beam splitter means for splitting said monochromatic radiation into said pair of beams.

18. Method of detecting submicron-dimensional particles in a fluid medium, and comprising the steps of;
   illuminating said medium with evanescent waves arising in a region of said fluid medium adjacent an interface between said fluid medium and a surface bounding another medium of higher refractive index through which a beam of exciting radiation is propagating by total reflection from, at least in part, said interface,
   detecting radiation emitted responsively to said evanescent waves by particles in Brownian motion in said region, and
   frequency analyzing modulation of the radiant emission created by motion of said particles across the boundary of said region.

19. Method as defined in claim 18 wherein the step of detecting comprises detecting scattering of said evanescent waves from said particles.

20. Method as defined in claim 18 wherein said beam of exciting radiation is selected to include wavelengths which are capable of exciting fluorescence in said particles.

21. Method as defined in claim 18 including the steps of staining said particles with a fluorescent stain, said illuminating being with evanescent waves arising from propagation of exciting radiation having excitation wavelengths of said stain.

22. Method as defined in claim 18 including the steps of staining said particles with a plurality of fluorescent stains each of which has a different characteristic fluorescent emission band, said illuminating being with evanescent waves arising from propagation of exciting radiation having excitation wavelengths of said stains, and
   wavelength filtering the radiation emitted by said particles so as to distinguish between fluorescence arising from different ones of said stains.

* * * * *